(12) United States Patent
Chen

(10) Patent No.: US 9,603,566 B2
(45) Date of Patent: Mar. 28, 2017

(54) SLEEP AWAKING SYSTEM AND METHOD

(71) Applicant: BOE TECHNOLOGY GROUP CO., LTD., Beijing (CN)

(72) Inventor: Ruisi Chen, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 0 days.

(21) Appl. No.: 14/648,479

(22) PCT Filed: Jan. 20, 2015

(86) PCT No.: PCT/CN2015/071099
§ 371 (c)(1),
(2) Date: May 29, 2015

(87) PCT Pub. No.: WO2016/045273
PCT Pub. Date: Mar. 31, 2016

(65) Prior Publication Data
US 2016/0081615 A1    Mar. 24, 2016

(30) Foreign Application Priority Data

Sep. 23, 2014 (CN) .......................... 2014 1 0489808

(51) Int. Cl.
*G08B 23/00* (2006.01)
*A61B 5/00* (2006.01)
(Continued)

(52) U.S. Cl.
CPC ............ *A61B 5/4809* (2013.01); *A61B 5/024* (2013.01); *A61B 5/11* (2013.01); *A61B 5/4812* (2013.01);
(Continued)

(58) Field of Classification Search
CPC ... A61B 5/4815; A61B 5/1116; A61B 5/1118; A61B 5/686; A61B 5/6826;
(Continued)

(56) References Cited

U.S. PATENT DOCUMENTS 5,101,831 A * 4/1992 Koyama ................ A61B 5/024
600/26
2002/0080035 A1 6/2002 Youdenko
(Continued)

FOREIGN PATENT DOCUMENTS

CN          1388921 A      1/2003
CN        102247122 A     11/2011
(Continued)

OTHER PUBLICATIONS

International Search Report and Written Opinion both dated Jun. 17, 2015; PCT/CN2015/071099.
(Continued)

*Primary Examiner* — Daniel Previl
(74) *Attorney, Agent, or Firm* — Ladas & Parry LLP

(57) ABSTRACT

Provided are a sleep awaking system and a sleep awaking method. The system comprises: a sign parameter collecting module for collecting a sign parameter of a human body; a time determining module for determining whether the present time is a REM determining time; a REM determining module for obtaining the sign parameter and determining whether the human body is in a REM stage according to the sign parameter in a REM determining period when the time determining module determines that the present time is the REM determining time; an awaking module for awaking the human body after a pre-awaking period when the REM determining module determines that the human body is in the REM stage and causing the human body to enter the REM stage within the pre-awaking period and awaking the (Continued)

human body after the pre-awaking period when the REM determining module determines that the human body is not in the REM stage, wherein the REM determining period and the pre-awaking period pass in turn from the REM determining time to the awaking time. The above system and method realize awaking the human body in the REM stage, making the human body feel a clear mind, act agilely, and full of spirit and energy after being awaked, which is good for health of the human body.

20 Claims, 6 Drawing Sheets

(51) Int. Cl.
  *A61B 5/024* (2006.01)
  *A61B 5/11* (2006.01)
  *A61M 21/02* (2006.01)
  *A61B 5/0205* (2006.01)
  *A61M 21/00* (2006.01)
  *A61B 5/01* (2006.01)
(52) U.S. Cl.
  CPC ............... *A61M 21/02* (2013.01); *A61B 5/01* (2013.01); *A61B 5/02055* (2013.01); *A61M 2021/0027* (2013.01); *A61M 2021/0044* (2013.01); *A61M 2021/0083* (2013.01); *A61M 2205/332* (2013.01); *A61M 2205/3303* (2013.01); *A61M 2230/06* (2013.01); *A61M 2230/50* (2013.01); *A61M 2230/63* (2013.01)
(58) Field of Classification Search
  CPC ............... A61B 5/0476; A61B 5/4812; A61B 2562/0219; A61B 5/0031; A61B 5/4818; A61B 5/02; A61B 5/0205; A61B 5/024; A61B 5/04
  USPC .. 340/575, 574, 573.4, 539.12, 539.15, 669, 340/691.3, 686.1, 815.45
  See application file for complete search history.

(56) References Cited

U.S. PATENT DOCUMENTS

| 2005/0190065 | A1* | 9/2005 | Ronnholm | A61M 21/00 340/575 |
| 2008/0180235 | A1* | 7/2008 | Chang | A61B 5/01 340/449 |
| 2011/0015495 | A1* | 1/2011 | Dothie | G06F 19/322 600/300 |
| 2011/0230790 | A1 | 9/2011 | Kozlov | |
| 2011/0291842 | A1 | 12/2011 | Oexman et al. | |
| 2012/0291785 | A1* | 11/2012 | Ramanan | A61M 16/0051 128/204.23 |
| 2013/0060097 | A1* | 3/2013 | Rubin | A61B 5/0476 600/301 |
| 2013/0163394 | A1* | 6/2013 | Loree, IV | G04G 11/00 368/256 |
| 2015/0163889 | A1* | 6/2015 | Godlieb | A61M 21/00 315/297 |

FOREIGN PATENT DOCUMENTS

| CN | 102596302 A | 7/2012 |
| CN | 202458887 U | 10/2012 |
| CN | 103167126 A | 6/2013 |
| CN | 103475971 A | 12/2013 |
| CN | 103750842 A | 4/2014 |
| CN | 203828910 U | 9/2014 |
| CN | 104257387 A | 1/2015 |
| WO | 2012/138233 A1 | 10/2012 |

OTHER PUBLICATIONS

First Chinese Office Action dated Jan. 26, 2016; Appln. No. 201410489808.0.

* cited by examiner

SLEEP AWAKING SYSTEM AND METHOD

TECHNICAL FIELD OF THE DISCLOSURE

The present disclosure relates to a sleep awaking system and a method thereof.

BACKGROUND

Scientific researches indicate that human's normal sleep structural period can be divided into two phases which are non-rapid eye movement (NREM) term and rapid eye movement (REM) term. The NREM and the REM appear alternately, and one alternation is called one sleep period. Each night usually has 4-5 sleep periods, and each period has 90-110 minutes.

During the NREM stage, the human body is in a sound sleep and deep sleep state. The brain wave has a low frequency and high amplitude, and presents a slowly varying curve. In addition, the eyeballs will not move rapidly. At this time, the sleep has large inertia, and the person is not easy to be awaked. If waking up from the NREM stage, a person will feel dizzy and sleepy, act slowly and be in a bad mood.

During the REM stage, the human body is in a shallow sleep state. The brain wave has a high frequency and low amplitude, and presents a saw tooth wave curve with distinctive features. The eyeballs move rapidly between right and left, the heart rate increases, and the breath is fast and irregular, the body temperature goes up, and dreams appear. Because the sleep is relatively shallow, the sleep inertia is small, and thus the person is easy to be awaked. If waking up from the REM stage, a person will feel a clear mind, act agilely, and be full of spirit and energy.

Existing alarm clocks awake a human body forcibly no matter in which sleep stage the human body is, which is very bad for human health if it acts in such a way for a long time.

SUMMARY

In order to overcome the above drawbacks in the prior art, embodiments of the present disclosure provides a sleep awaking system and method thereof to realize the function of awaking a human body in the REM stage.

A sleep awaking system comprises: a sign parameter collecting module for collecting a sign parameter of a human body; a time determining module for determining whether the present time is a REM determining time; a REM determining module for obtaining the sign parameter and determining whether the human body is in a REM stage according to the sign parameter in a REM determining period when the time determining module determines that the present time is the REM determining time; an awaking module for awaking the human body after a pre-awaking period when the REM determining module determines that the human body is in the REM stage and causing the human body to enter the REM stage within the pre-awaking period and awaking the human body after the pre-awaking period when the REM determining module determines that the human body is not in the REM stage, wherein the REM determining period and the pre-awaking period pass in turn from the REM determining time to the awaking time.

Alternatively, the sign parameter collecting module comprises an acceleration collecting unit for collecting acceleration signals of body movement.

Alternatively, the REM determining module comprises: a sleep/wake determining unit for obtaining acceleration signals of respective times within the REM determining period when the time determining module determines that the present time is the REM determining time, calculating the total variation of the acceleration signals within the REM determining period, and comparing the total variation of the acceleration signals with a threshold for the total variation of the acceleration signals within the REM determining period, determining that the human body is in a sleep state when the total variation of the acceleration signals is smaller than or equal to the threshold for the total variation of the acceleration signals, and determining that the human body is in a wake state when the total variation of the acceleration signals is larger than the threshold for the total variation of the acceleration signals; and a REM determining unit for calculating variations of acceleration signals at adjacent times within the REM determining period when the sleep/wake determining unit determines that the human body is in the sleep state, comparing the variations of the acceleration signals with a threshold for the variations of the acceleration signals one by one, determining whether variation of the acceleration signals is periodic, and determining that the human body is in the REM stage when at least one variation of the acceleration signals is larger than the threshold for the variations of the acceleration signals at adjacent times and/or the variation of the acceleration signals is not periodic, and determining that the human body is not in the REM stage when all the variations of the acceleration signals are smaller than or equal to the threshold for the variations of the acceleration signals at adjacent times and the variation of the acceleration signals is periodic.

Alternatively, the sign parameter collecting module further comprises a heart rate collecting unit for collecting heart rate signals; the sleep/wake determining unit of the REM determining module is configured to obtain heart rate signals of respective times within the REM determining period, calculate the average of the heart rate signals within the REM determining period when the time determining module determines that the present time is the REM determining time, compare the average of the heart rate signals with a threshold for the average of the heart rate signals within the REM determining period, determine that the human body is in the sleep state when the average of the heart rate signals is smaller than or equal to the threshold for the average of the heart rate signals and the total variation of the acceleration signals is smaller than or equal to the threshold for the total variation of the acceleration signals, and determine that the human body is in a wake state when the average of the heart rate signals is larger than the threshold for the average of the heart rate signals and/or the total variation of the acceleration signals is larger than the threshold for the total variation of the acceleration signals; and the REM determining unit of the REM determining module is configured to, when the sleep/wake determining unit determines that the human body is in the seep state, calculate variations of the heart rate signals at adjacent times within the REM determining period, compare the variations of the heart rate signals with a threshold for the variations of the heart rate signals at adjacent times one by one, determine whether variation of the heart rate signals is periodic, determine the human body is in the REM stage when any one or more of the determination results of the four determinations that at least one variation of the heart rate signals is larger than the threshold for the variations of the heart rate signals at adjacent times, that the variation of the heart rate signals is not periodic, that at least one variation of the acceleration signals is larger than the threshold for the variations of the acceleration signals at adjacent times and that the variation of the acceleration signals is not periodic is true, and determine that the human body is not in the REM stage when all the variations of the heart rate signals are smaller than or equal to the threshold for the variations of the heart rate signals at adjacent times, all the variations of the acceleration signals are smaller than or equal to the threshold for the variations of the acceleration signals at adjacent times, and the variation of the heart rate signals and the variation of the acceleration signals are both periodic.

Alternatively, the sign parameter collecting module further comprises a body temperature collecting unit for collecting body temperature signals; and the REM determining unit of the REM determining module is configured to obtain a variation curve of the body temperature signals with respect to time within the REM determining period when the time determining module determines that the present time is the REM determining time, calculate a difference degree between the variation curve of the body temperature signals with respect to time and the ideal variation curve of the body temperature signals of the human body in the REM stage with respective to time, determine the human body is in the REM stage when any one or more of the determination results of the five determinations that the difference degree is smaller than or equal to a threshold for the difference degree, that at least one variation of the acceleration signals is larger than the threshold for the variations of the acceleration signals at adjacent times, that the variation of the acceleration signals is not periodic, that at least one variation of the heart rate signals is larger than the threshold for the variations of the heart rate signals at adjacent times and that the variation of the heart rate signals is not periodic is true, and determine that the human body is not in the REM stage when the difference degree is larger than the threshold for the difference degree, all the variations of the acceleration signals are smaller than or equal to the threshold for the variations of the acceleration signals at adjacent times, all the variations of the heart rate signals are smaller than or equal to the threshold for the variations of the heart rate signals at adjacent times, and the variation of the heart rate signals and the variation of the acceleration signals are both periodic.

Alternatively, an awaking buffering period is included after the REM determining period and the pre-awaking period pass in turn from the REM determining time to the awaking time, the time length from the REM determining time to the awaking time is equal to the sum of the REM determining period, the pre-awaking period and the awaking buffering period.

Alternatively, the awaking module comprises: a white light emitting unit for emitting white light changing gradually from weak to strong within the awaking buffering period after the pre-awaking period until the human body is awaked or the awaking buffering period is over and stopping emitting the white light changing gradually from weak to strong then; a blue light emitting unit for, when the REM determining module determines that the human body is not in the REM stage, emitting blue light changing gradually from weak to strong within the pre-awaking period to cause the human body to enter the REM stage until the pre-awaking period is over, and stopping emitting the blue light changing gradually from weak to strong then; and a sound generating unit for generating a sound to awake the human body when the human body is not awaked at the end of the awaking buffering period.

Alternatively, the sleep/wake determining unit of the REM determining module is also configured to determine whether the human body is in the sleep state or the wake state within the awaking buffering period, and trigger the white light emitting unit to stop emitting the white light changing gradually from weak to strong when it is determined that the human body is in the wake state.

Alternatively, wherein the time length of the REM determining period is 8 minutes~12 minutes, the time length of the pre-awaking period is 15 minutes~25 minutes, and the time length of the awaking buffering period is 10 minutes~20 minutes.

Alternatively, the time length from the REM determining time to the awaking time is equal to the sum of the REM determining period and the pre-awaking period.

An embodiment of the present disclosure also provides a sleep awaking method comprising: a step S1 of collecting a sign parameter of a human body; a step S2 of determining whether the present time is a REM determining time, and entering a step S3 if yes; the step S3 of obtaining the sign parameter, determining whether the human body is in a REM stage according to the sign parameter within the REM determining period, entering a step S4 if yes, and entering a step S5 if no; the step S4 of awaking the human body after a pre-awaking period; the step S5 of causing the human body to enter the REM stage within the pre-awaking period, and awaking the human body after the pre-awaking period, wherein the REM determining period and the pre-awaking period pass in turn from the REM determining time to the awaking time.

Alternatively, the step S1 comprises collecting acceleration signals of body movement.

Alternatively, the step S3 comprises: a step S31 of obtaining acceleration signals of respective times within the REM determining period, calculating the total variation of the acceleration signals within the REM determining period, comparing the total variation of the acceleration signals with a threshold for the total variation of the acceleration signals within the REM determining period, determining that the human body is in a sleep state and entering a step S32 when the total variation of the acceleration signals is smaller than or equal to the threshold for the total variation of the acceleration signals, and determining that the human body is in a wake state when the total variation of the acceleration signals is larger than the threshold for the total variation of the acceleration signals; and the step S32 of calculating variations of acceleration signals at adjacent times within the REM determining period, comparing the variations of the acceleration signals with a threshold for the variations of the acceleration signals at adjacent times one by one, determining whether variation of the acceleration signals is periodic, determining that the human body is in the REM stage and entering the step S4 when at least one variation of the acceleration signals is larger than the threshold for the variations of the acceleration signals at adjacent times and/or the variation of the acceleration signals is not periodic, and determining that the human body is not in the REM stage and entering the step S5 when all the variations of the acceleration signals are smaller than or equal to the threshold for the variations of the acceleration signals at adjacent times and the variation of the acceleration signals is periodic.

Alternatively, the step S1 further comprises collecting heart rate signals; the step S31 comprises: obtaining heart rate signals of respective times within the REM determining period, calculating the average of the heart rate signals within the REM determining period, comparing the average of the heart rate signals with a threshold for the average of the heart rate signals within the REM determining period, determining that the human body is in the sleep state and entering the step S32 when the average of the heart rate signals is smaller than or equal to the threshold for the average of the heart rate signals and the total variation of the acceleration signals is smaller than or equal to the threshold for the total variation of the acceleration signals, and determine that the human body is in a wake state when the average of the heart rate signals is larger than the threshold for the average of the heart rate signals and/or the total variation of the acceleration signals is larger than the threshold for the total variation of the acceleration signals; and the step S32 comprises: calculating variations of the heart rate signals at adjacent times within the REM determining period, comparing the variations of the heart rate signals with a threshold for the variations of the heart rate signals at adjacent times one by one, determining whether variation of the heart rate signals is periodic, determining that the human body is in the REM stage and entering the step S4 if any one or more of the determination results of the four determinations that at least one variation of the heart rate signals is larger than the threshold for the variations of the heart rate signals at adjacent times, that the variation of the heart rate signals is not periodic, that at least one variation of the acceleration signals is larger than the threshold for the variations of the acceleration signals at adjacent times and that the variation of the acceleration signals is not periodic is true, and determining that the human body is not in the REM stage and entering the step S5 if all the variations of the heart rate signals are smaller than or equal to the threshold for the variations of the heart rate signals at adjacent times, all the variations of the acceleration signals are smaller than or equal to the threshold for the variations of the acceleration signals at adjacent times, and the variation of the heart rate signals and the variation of the acceleration signals are both periodic.

Alternatively, the step S1 further comprises collecting body temperature signals; and the step S32 comprises: obtaining a variation curve of the body temperature signals with respect to time within the REM determining period, calculating a difference degree between the variation curve of the body temperature signals with respect to time and the ideal variation curve of the body temperature signals of the human body in the REM stage with respective to time, determining the human body is in the REM stage and entering the step S4 when any one or more of the determination results of the five determinations that the difference degree is smaller than or equal to a threshold for the difference degree, that at least one variation of the acceleration signals is larger than the threshold for the variations of the acceleration signals at adjacent times, that the variation of the acceleration signals is not periodic, that at least one variation of the heart rate signals is larger than the threshold for the variations of the heart rate signals at adjacent times and that the variation of the heart rate signals is not periodic is true, and determine that the human body is not in the REM stage and entering the step S5 when the difference degree is larger than the threshold for the difference degree, all the variations of the acceleration signals are smaller than or equal to the threshold for the variations of the acceleration signals at adjacent times, all the variations of the heart rate signals are smaller than or equal to the threshold for the variations of the heart rate signals at adjacent times, and the variation of the heart rate signals and the variation of the acceleration signals are both periodic.

Alternatively, an awaking buffering period is included after the REM determining period and the pre-awaking period pass in turn from the REM determining time to the awaking time, the time length from the REM determining time to the awaking time is equal to the sum of the REM determining period, the pre-awaking period and the awaking buffering period.

Alternatively, the step S4 comprises: emitting white light changing gradually from weak to strong within the awaking buffering period after the pre-awaking period until the human body is awaked or the awaking buffering period is over and stopping emitting the white light changing gradually from weak to strong then; and generating a sound to awake the human body if the human body is not awaked at the end of the awaking buffering period; the step S5 comprises: emitting blue light changing gradually from weak to strong within the pre-awaking period to cause the human body to enter the REM stage until the pre-awaking period is over, and stopping emitting the blue light changing gradually from weak to strong then; emitting white light changing gradually from weak to strong within the awaking buffering period until the human body is awaked or the awaking buffering period is over and stopping emitting the white light changing gradually from weak to strong then; and generating a sound to awake the human body if the human body is not awaked at the end of the awaking buffering period.

Alternatively, the step S4 further comprises: determining whether the human body is in the sleep state or the wake state within the awaking buffering period, and stopping emitting the white light changing gradually from weak to strong when it is determined that the human body is in the wake state.

Alternatively, the time length of the REM determining period is 8 minutes~12 minutes, the time length of the pre-awaking period is 15 minutes~25 minutes, and the time length of the awaking buffering period is 10 minutes~20 minutes.

Alternatively, the time length from the REM determining time to the awaking time is equal to the sum of the REM determining period and the pre-awaking period.

In the sleep awaking system and method provided by the present disclosure, by setting a sign parameter collecting module, a time determining module, a REM determining module and awaking module, the REM determining module determines at a time (i.e. the REM determining time) before the awaking time whether the human body is in the REM stage according to the sign parameter of the human body collected by the sign parameter collecting module. If yes, the awaking module awakes the human body; if no, the awaking module causes the human body into the REM stage, and then awakes the human body, such as to realize the purpose of awaking the human body in the REM stage, making the human body feel a clear mind, act agilely, and full of spirit and energy after being awaked, which is good for health of the human body.

DETAILED DESCRIPTION

In order to make the above features and advantages of the present disclosure more clear and easily understood, the technical solutions of embodiments of the present disclosure will be clearly and completely described in connection with the figures in the embodiments of the present disclosure below.

Figure 1:
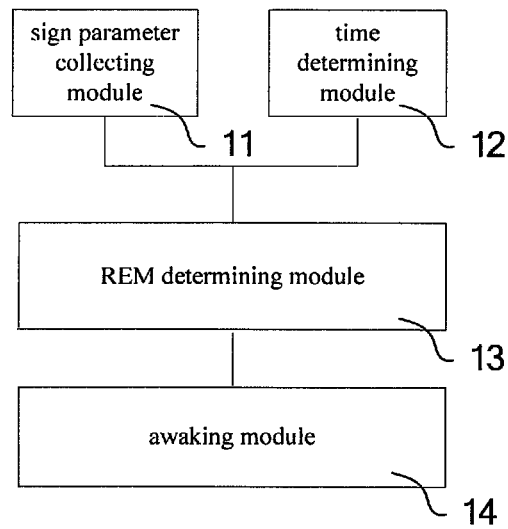
FIG. 1 is a schematic diagram of a structure of a sleep awaking system provided by an embodiment of the present disclosure.

FIG. 1 illustrates a schematic diagram of a structure of a sleep awaking system provided by an embodiment of the present disclosure. As shown in FIG. 1, the sleep awaking system comprises: a sign parameter collecting module 11 for collecting a sign parameter of a human body; a time determining module 12 for determining whether the present time is a REM determining time; a REM determining module 13 for obtaining the sign parameter and determining whether the human body is in a REM stage according to the sign parameter in a REM determining period when the time determining module 12 determines that the present time is the REM determining time; and an awaking module 14 for awaking the human body after a pre-awaking period when the REM determining module 13 determines that the human body is in the REM stage, and facilitating the human body to enter the REM stage within the pre-awaking period, and awaking the human body after the pre-awaking period, when the REM determining module determines that the human body is not in the REM stage.

It is noted that the REM determining period and the pre-awaking period pass through in turn from the REM determining time to the awaking time. Whether the human body is in the REM stage is determined in the REM determining period. If it is determined that the human body is not in the REM stage, the human body is facilitated to enter the REM stage in the pre-awaking period to awake the human body from the REM stage.

In the above sleep awaking system, by setting the sign parameter collecting module 11, the time determining module 12, the REM determining module 13 and the awaking module 14, the function of awaking the human body from the REM stage is realized. Since the human body is in the shallow sleep state, has small sleep inertia and is easily awaked in the REM stage, the sleep awaking system provided by the present embodiment enables the human body to feel a clear mind, act agilely, and be full of spirit and energy after being awaked.

Factors such as breath and heart beat can cause the human body to generate small movement in space (axis x, axis y and axis z) even if the human body is static. Since the human body has different breath frequencies and speeds and different heart beat speeds in the REM stage and the NREM stage of the sleep stage and the wake stage, it is possible to know which state the human body is in by testing the acceleration of the body movement of the human body. Furthermore, factors such as heart rate and body temperature can also reflect the state of the human body. Therefore, the sign parameter of the human body in the present embodiment can exemplarily comprise acceleration of body movement, heart rate, body temperature, or the like of the human body.

Figure 2:
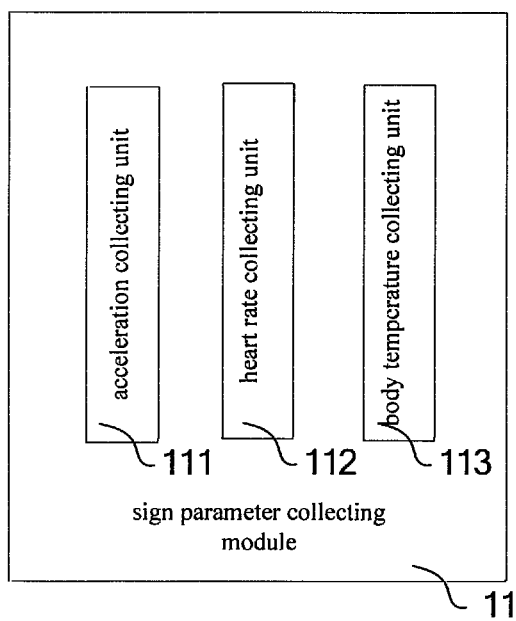
FIG. 2 is a schematic diagram of a structure of a sign parameter collecting module in a sleep awaking system provided by an embodiment of the present disclosure.

FIG. 2 illustrates a schematic diagram of a structure of the sign collecting module in the above sleep awaking system. As shown in FIG. 2, the above sign parameter collecting module 11 can exemplarily comprise an acceleration collecting unit 111 for collecting acceleration signals of body movement to take the collected acceleration signals as a base for determining whether the human body is in the sleep or wake state, or in the REM or NREM stage. The above sign parameter collecting module 11 can further comprise: a heart rate collecting unit 112 for collecting heart rate signals and/or a body temperature collecting unit 113 for collecting body temperature signals to provide more references for determining whether the human body is in the sleep or wake state, or in the REM or NREM stage thereby making the determination result more accurate.

It is noted that the collecting of the sign parameters by the sign parameter collecting module 11 can be in real time in order to provide sign parameters at any time and raise the processing speed of the system, can also be periodic in order to save power consumption of the system, and can further be under the control of a processor or triggered by another component for sign parameters in order to save power consumption of the system as much as possible.

Figure 3:
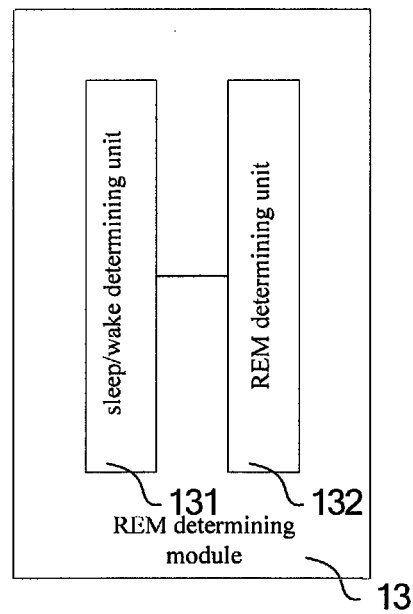
FIG. 3 is a schematic diagram of a structure of a REM determining module in a sleep awaking system provided by an embodiment of the present disclosure.

FIG. 3 illustrates a schematic diagram of a structure of the REM determining module in the above sleep awaking system. As shown in FIG. 3, in the present embodiment, the REM determining module 13 can exemplarily comprise a sleep/wake determining unit 131 and a REM determining unit 132 connected thereto.

Here, the sleep/wake determining unit 131 is configure to determine whether the human body is in the sleep state or the wake state when the time reaches the REM determining time before the awaking time. Specifically, the determination procedure can be: when the time determining module 12 determines that the present time is the REM determining time, obtaining acceleration signals of respective times within the REM determining period, wherein the acceleration signals comprises an acceleration signal at the REM time and an acceleration signal at the end of the REM determining period, calculating the difference between the acceleration signal at the REM time and the acceleration signal at the end of the REM determining period to obtain the total variation of the acceleration signals within the REM determining period, comparing the total variation of the acceleration signals with a threshold for the total variation of the acceleration signals within the REM determining period, determining that the human body is in the sleep state when the total variation of the acceleration signals is smaller than or equal to the threshold for the total variation of the acceleration signals, determining that the human body is in the wake state when the total variation of the acceleration signals is larger than the threshold for the total variation of the acceleration signals within the REM determining period.

It is noted that the difference between the acceleration signal at the REM determining time and the acceleration signal at the end of the REM determining period is the actual total variation of the acceleration within the REM determining period. If the actual total variation is smaller than or equal to a threshold for the total variation of the acceleration within the same period, it means that the human body has small variation of body movement within the period and the human body is in the sleep state; otherwise, it means that the human body is in the wake state. The time length of the REM determining period can be preferably 8 minutes~12 minutes, or can be 10 minutes. The user can also set the time length according to his own condition. The threshold for the total variation of the acceleration signals within the REM determining period is determined according to the acceleration value when the human body is at the verge between the sleep state and the wake state in a time period whose time length is equal to the REM determining period, obtained by the observation in the scientific research.

In addition, when the sleep/wake determining unit 131 determines whether the human body is in the sleep state, it is also possible to obtain heart rate signals at respective times within the REM determining period, and calculate the average of the heart rates within the period. Because the average heart rate when the human body is in the sleep state is smaller than that in the wake state, it is possible to compare the calculated average of the heart rates with a threshold for the average of heart rate signals within the REM determining period. If the calculated average of the heart rate signals is smaller than or equal to the threshold for the average of the heart rate signals within the REM determining period and the total variation of the acceleration signals is smaller than or equal to the threshold for the total variation of the acceleration signals, it is determined that the human body is in the sleep state. If the calculated average of the heart rate signals is larger than the threshold for the average of the heart rate signals and/or the total variation of the acceleration signals is larger than the threshold for the total variation of the acceleration signals, it is determined that the human body is in a wake state. Therefore, the determination accuracy of the sleep/wake determining unit 131 can be improved. The threshold for the average of the heart rate signals is determined according to the average of the heart rate when the human body is at the verge between the sleep state and the wake state in a time period whose time length is equal to the REM determining period obtained by the observation in the scientific research.

Further, the temperature of the human body in different stages of the seep state and the wake state has a variation curve. Therefore, it is also possible to obtain temperatures at respective times within the REM determining period when the sleep/wake determining unit 131 determines whether the human body is in the sleep state, and compare the obtained temperature variation curve with the ideal temperature variation curve to be able to obtain information on which state and which stage the human body is in and take it as a reference for determining whether the human body is in the sleep state or wake state, thereby further raising the determination accuracy of the sleep/wake determining unit 131.

It is noted that, if the sleep/wake determining unit 131 determines that the human body is in the wake state, it means that it is not necessary to perform awaking operation on the human body, and the sleep awaking system can be made stopping operation automatically.

The REM determining unit 132 is configured to determine whether the human body is in the REM stage of the sleep according to acceleration values at respective times within the REM determining period when the human body is determined to be in the sleep state. The determination procedure can exemplarily be: when the sleep determining unit 131 determines that the human body is in the sleep state, calculating variations of acceleration signals at adjacent times according to the obtained acceleration signals at respective times within the REM determining period, comparing the variations of the acceleration signals with a threshold for the variations of the acceleration signals at adjacent times one by one, and determining whether variation of the acceleration signals is periodic; when at least one variation of the acceleration signals is larger than the threshold for the variations of the acceleration signals at adjacent times and/or the variation of the acceleration signals is not periodic, determining that the human body is in the REM stage; and when the variations of the acceleration signals are all smaller than or equal to the threshold for the variations of the acceleration signals at adjacent times and the variation of the acceleration signals is periodic, determining that the human body is not in the REM stage.

It is noted that the variation of the acceleration signal at adjacent times is the variation of the acceleration at the present time relative to the acceleration at the previous time, and it reflects the variation situation of the acceleration within the REM determining period. Only if multiple variations obtained by calculation are all smaller than or equal to the threshold for variations of the acceleration signals at adjacent times and the variation of the acceleration signal is periodic, it means that the human body's sign, the breath frequency is stable, the sleep is deeper, among others, and thus the human body is in the deep sleep phase, that is, not in the REM state. On the contrary, as long as there is one variation is larger than the threshold for the variation of the acceleration signals at adjacent times and/or the variation of the acceleration is not periodic, it means that the human body's sign is not stable, and thus the human body is in the shallow sleep stage, i.e., the REM stage. The threshold for the average of the acceleration signals at adjacent times is determined by the variation situation of the acceleration when the human body is at the verge between the sleep state and the wake state obtained according to the observation in the scientific research.

If the collected sign parameters comprise a heart rate signal, it is possible to take the heart rate signal as reference data for determining the human body is in the REM stage to raise the accuracy of determination. Specifically, when the sleep/wake determining unit 131 determines that the human body is in the seep state, the REM determining unit 132 of the REM determining module 13 can calculate variations of the heart rate signals at adjacent times within the REM determining period, compare the variations of the heart rate signals with a threshold for the variations of the heart rate signals at adjacent times one by one, and determine whether variation of the heart rate signals is periodic. If any one or more of the determination results of the four determinations that at least one variation of the heart rate signals is larger than the threshold for the variations of the heart rate signals at adjacent times, that the variation of the heart rate signals is not periodic, that at least one variation of the acceleration signals is larger than the threshold for the variations of the acceleration signals at adjacent times, and that the variation of the acceleration signals is not periodic is true, it is determined that the human body is in the REM stage. If all the variations of the heart rate signals are smaller than or equal to the threshold for the variations of the heart rate signals at adjacent times, all the variations of the acceleration signals are smaller than or equal to the threshold for the variations of the acceleration signals at adjacent times, and the variation of the heart rate signals and the variation of the acceleration signals are both periodic, it is determined that the human body is not in the REM stage.

For taking three sign parameters that are acceleration, heart rate and body temperature as determination bases of the REM stage, for example, when the time determining module 12 determines that the present time is the REM determining time, the REM determining unit 132 of the REM determining module 13 can obtain a variation curve of the body temperature signals with respect to time within the REM determining period, calculate a difference degree between the variation curve of the body temperature signals with respect to time and the ideal variation curve of the body temperature signals of the human body in the REM stage with respective to time, determine the human body is in the REM stage when any one or more of the determination results of the five determinations that the difference degree is smaller than or equal to a threshold for the difference degree, that at least one variation of the acceleration signals is larger than the threshold for the variations of the acceleration signals at adjacent times, that the variation of the acceleration signals is not periodic, that at least one variation of the heart rate signals is larger than the threshold for the variations of the heart rate signals at adjacent times and that the variation of the heart rate signals is not periodic is true, and determine that the human body is not in the REM stage when the difference degree is larger than the threshold for the difference degree, all the variations of the acceleration signals are smaller than or equal to the threshold for the variations of the acceleration signals at adjacent times, all the variations of the heart rate signals are smaller than or equal to the threshold for the variations of the heart rate signals at adjacent times, and the variation of the heart rate signals and the variation of the acceleration signals are both periodic. Therefore, the determination accuracy of the REM is further improved.

It is noted that, in the present embodiment, it is possible to connect the REM determining module 13 directly with the sign parameter collecting module 11 and the time determining module 12 respectively so that when the time determining module 12 determines that the present time is the REM determining time, the required signal parameter can be directly obtained from the sign parameter collecting module 11 in order to perform determination. Alternatively, it is also possible to connect the sign parameter collecting module 11, the time determining module 12 and the REM determining module 13 in turn, such that the sign parameter collecting module 11 sends the sign parameter to the time determining module 12 after collecting the sign parameter, then the time determining module 12 determines whether the present time is the REM determining time, if it is yes, sends the received sign parameter to the REM determining module 13, and if it is no, does not send the received sign parameter but perform the determination for the next time point.

Figure 5:
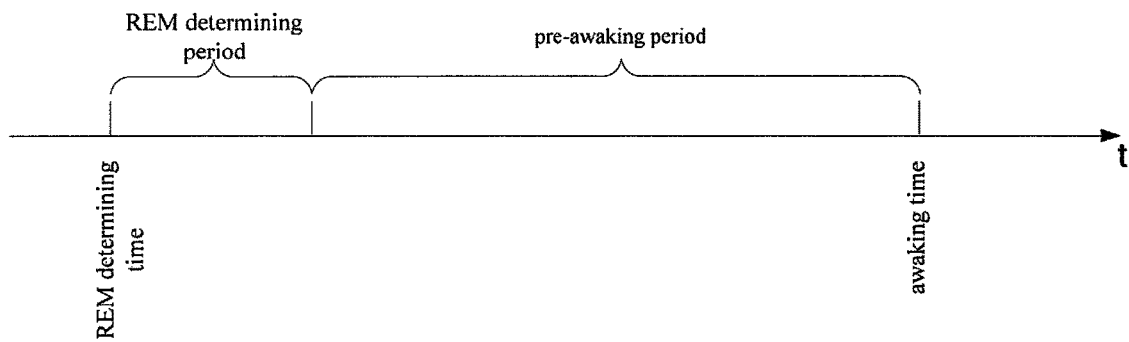
FIG. 5 is a timing diagram of an operation of a sleep awaking system provided by an embodiment of the present disclosure.

FIG. 5 schematically illustrates an operation time sequence of the sleep awaking system provided by the present embodiment. As shown in FIG. 5, the time length from the REM determining time to the awaking time is equal to the sum of the REM determining period and the pre-awaking period. In the REM determining period, it is determined whether the human body is in the REM stage. After the determination is completed, the awaking module 14 performs awaking operation on the human body within the pre-awaking period to awake the human body in time according to the awaking time set by the user.

Figure 6:
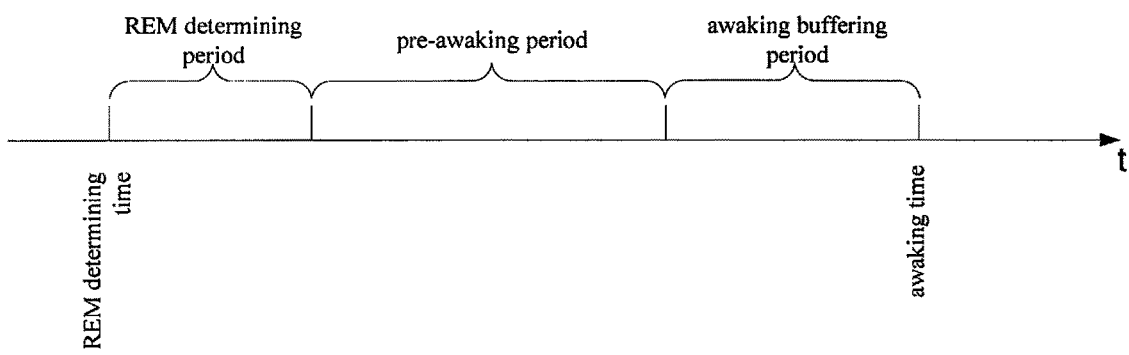
FIG. 6 is another timing diagram of an operation of a sleep awaking system provided by an embodiment of the present disclosure.

The scientific research shows that awaking the human body by gradually changing light is gentler than the conventional sound manner, and makes the person feel comfortable after being waked up. Based on this, the awaking module 14 in the present embodiment can use the manner of light awaking to perform awaking operation on the human body. In this case, the operation time sequence of the sleep awaking system provided by the present embodiment can be as shown in FIG. 6. FIG. 6 schematically illustrates another operation timing diagram of the sleep awaking system. As shown in FIG. 6, an awaking buffering period is included after the REM determining period and the pre-awaking period pass in turn from the REM determining time to the awaking time, the time length from the REM determining time to the awaking time is equal to the sum of the REM determining period, the pre-awaking period and the awaking buffering period. Because the manner of light awaking is gentler, the procedure in which the human body is awaked by light is a gradually changing procedure, and thus the setting of the awaking buffering period can ensure the timeliness of the awaking.

It is noted that the time lengths of the awaking buffering period and the pre-awaking period are not specifically limited, but can be set according to practical situations. The time length of the pre-awaking period can exemplarily be 15 minutes~25 minutes, or can also be 20 minutes, in order to ensure the human body can enter the REM stage within this period as far as possible. The time length of the awaking buffering period can exemplarily be 10 minutes~20 minutes, or can also be 15 minutes, in order to ensure that the human body can be awaked by light gradually.

Figure 4:
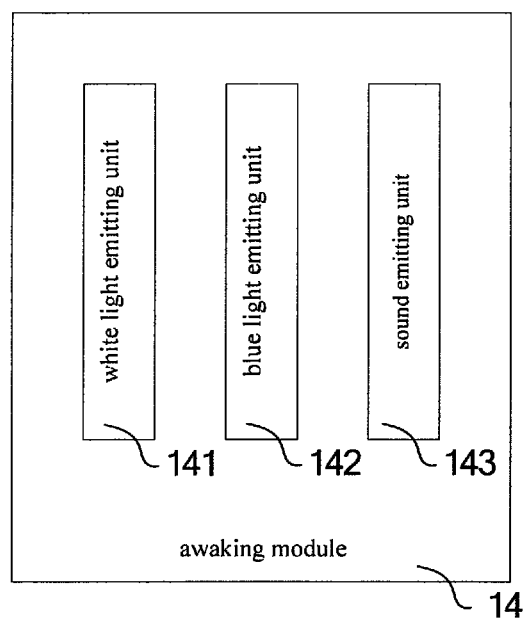
FIG. 4 is a schematic diagram of a structure of an awaking module in a sleep awaking system provided by an embodiment of the present disclosure.

FIG. 4 illustrates a schematic structural diagram of the awaking module in the sleep awaking system provided in an embodiment of the present disclosure. As shown in FIG. 4, the awaking module 14 can exemplarily comprise a white light emitting unit 141, a blue light emitting unit 142 and a sound generating unit 143.

Herein, the white light emitting unit 141 is configured to emit white light changing gradually from weak to strong in order to awake the human body gradually when the human body is in the REM stage. The operation procedure of the white light generating unit 141 can specifically be: when the REM determining module 13 determines that the human body is in the REM stage, emitting white light changing gradually from weak to strong within the awaking buffering period after the pre-awaking period until the human body is awaked or the awaking buffering period is over, and stopping emitting the white light changing gradually from weak to strong then.

It is noted that, in the procedure that the white emitting unit 141 emits white light to perform awaking operation, it is possible to use the sleep/awaking determining unit 131 of the REM determining module 13 to obtain the sign parameters of the human body continuously in order to perform determination of sleep or wake on the human body until the sleep/wake determining unit 131 determines that the human body is in the wake state within the awaking buffering period, and then trigger the white light emitting unit 141 to stop emitting the white light changing gradually from weak to strong and make the system stop operating.

The blue light emitting unit 142 is used to emit blue light changing gradually from weak to strong when the human body is not in the REM stage to lead the human body to the REM stage gradually in order for the white light emitting unit 141 to perform the awaking operation. The operation procedure of the blue light emitting unit 142 can be specifically described as following: when the REM determining module 13 determines that the human body is not in the REM stage, emitting blue light changing gradually from weak to strong within the pre-awaking period to cause the human body to enter the REM stage until the pre-awaking period is over, and stopping emitting the blue light changing gradually from weak to strong then.

It is noted that, the gradually changing blue light can control the release of melatonin of the human body. The melatonin has the function of promoting the sleep of the human body; therefore, the emitting of the blue light changing gradually from weak to strong can lead the human body in the deep sleep state into the REM stage gradually.

In the procedure that the blue light emitting unit 142 emits blue light to cause the human body to enter the REM stage, it is possible to use the REM determining module 13 to perform determination on whether the human body is in the REM stage until the human body enters the REM stage within the pre-waking period.

The sound generating unit 143 is configured to generate a sound to awake the human body when the human body is not awaked at the end of the awaking buffering period, such as to effectively ensure the user is waked up in time at the awaking time.

Figure 7:
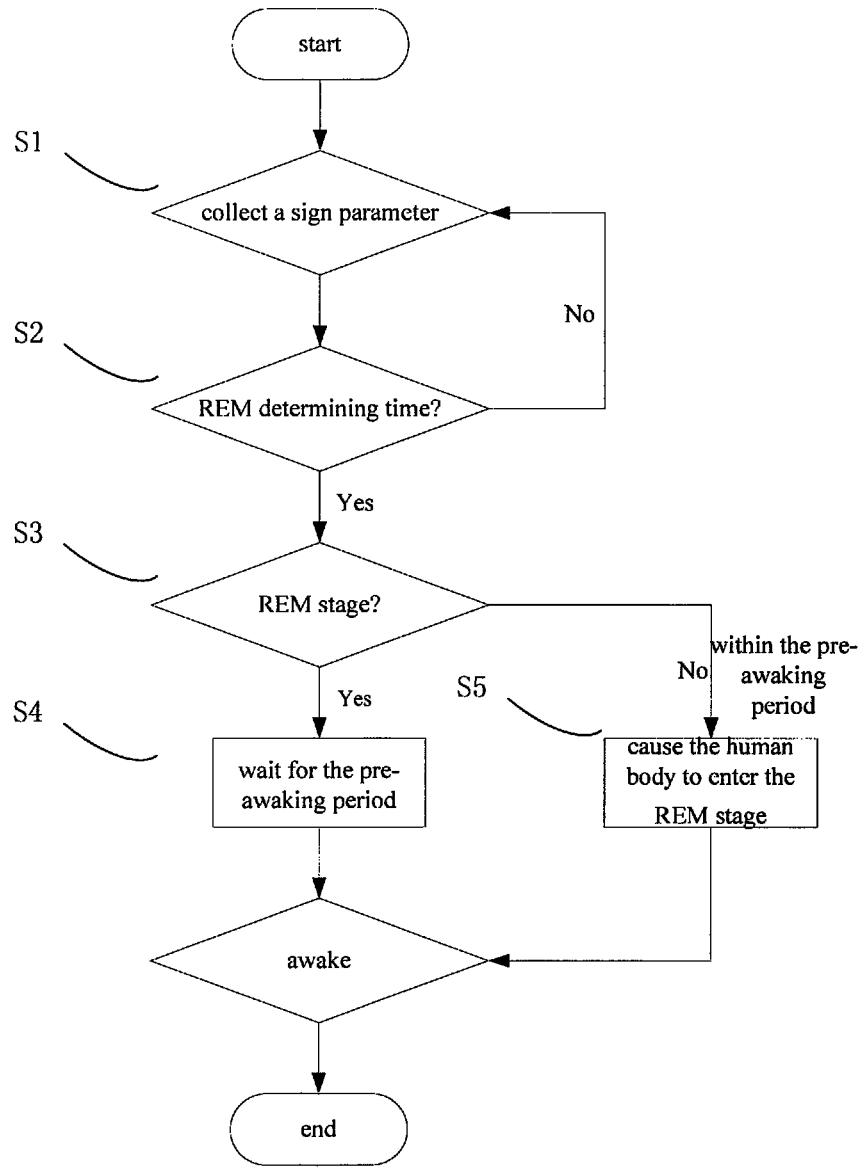
FIG. 7 is a flowchart of a sleep awaking method provided by an embodiment of the present disclosure.

FIG. 7 illustrates a flow chart of a sleep awaking method based on the sleep awaking system provided by the above embodiment. As shown in FIG. 7, the method comprises the following steps:

a step S1 of collecting a sign parameter of a human body;

a step S2 of determining whether the present time is a REM determining time, and entering a step S3 if yes;

the step S3 of obtaining the sign parameter, determining whether the human body is in a REM stage according to the sign parameter within the REM determining period, entering a step S4 if yes, and entering a step S5 if no;

the step S4 of awaking the human body after a pre-awaking period;

the step S5 of causing the human body to enter the REM stage within the pre-awaking period, and awaking the human body after the pre-awaking period.

Herein the REM determining period and the pre-awaking period pass in turn from the REM determining time to the awaking time.

By the above sleep awaking method, the human body can be awaked from the REM stage. Since the human body is in the shallow sleep state, has small sleep inertia and is easily awaked in the REM stage, the sleep awaking method provided by the present embodiment enables the human body to feel a clear mind, act agilely, and be full of spirit and energy after being awaked.

Alternatively, when it is determined that the present time is not the REM determining time, it can return to the step S1 to continue the collecting of the sign parameter.

Depending on different sign parameters required by the REM determination, the above step S1 can comprise collecting acceleration signals of body movement, and the step can also comprise collecting heart rate signals and/or collecting body temperature signals.

In order to determine whether the human body is in the REM stage, it is needed to first determine whether the human body is in the sleep state, and then determine whether the human body is in the REM stage.

Figure 8:
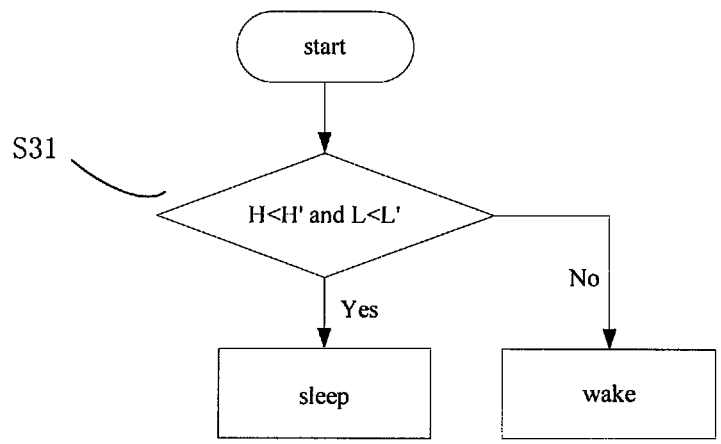
FIG. 8 is a flowchart for determining sleep or wake in a sleep awaking method provided by an embodiment of the present disclosure.

FIG. 8 illustrates a flow chart for determining sleep or wake in the sleep awaking method. Specifically, as shown in FIG. 8, the above step S3 can comprise the following steps:

a step S31 of obtaining acceleration signals of respective times within the REM determining period, in which the acceleration signals comprises an acceleration signal at the REM determining time and an acceleration signal at the end of the REM determining period, calculating the difference H between the acceleration signal at the REM determining time and the acceleration signal at the end of the REM determining period, comparing H with a threshold H' for the total variation of the acceleration signals within the REM determining period, determining that the human body is in the sleep state and entering a step S32 when the difference H is smaller than or equal to the threshold H' for the total variation of the acceleration signals within the REM determining period, determining that the human body is in the wake state when the difference H is larger than the threshold H' for the total variation of the acceleration signals within the REM determining period.

Figure 9:
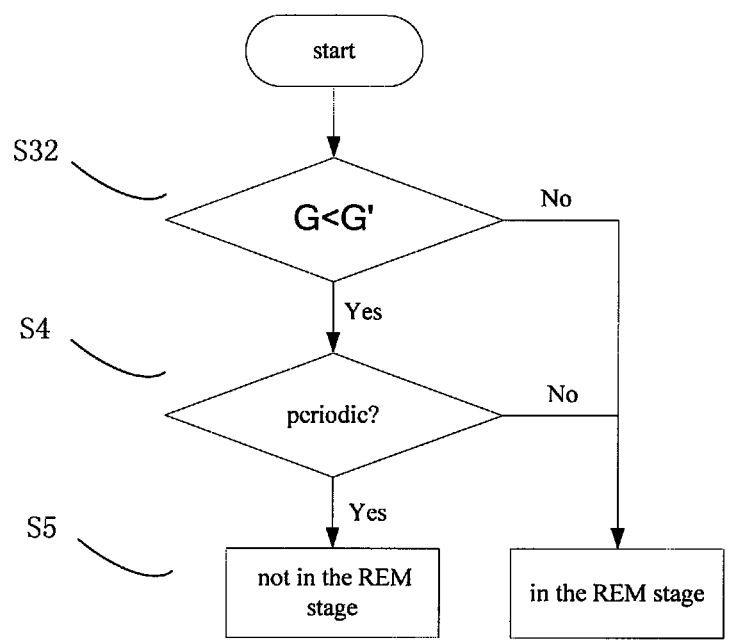
FIG. 9 is a flowchart for determining whether it is in the REM stage in a sleep awaking method provided by an embodiment of the present disclosure.

Alternatively, in the determination procedure described in the above step S31, it is possible to additionally judge some determination conditions to improve the determination accuracy. For example, it is possible to calculate the average L of the heart rates within the REM determining period, compare the average L of the heart rates with a threshold L' of the average of the heart rates, determine the sleep state when $H \leq H'$ and $L \leq L'$, and determine the wake state when $H > H'$ and/or $L > L'$. As another example, it is also possible to add a determination condition related to body temperature (details can refer to the related descriptions in the first embodiment) to further improve the accuracy of the determination of sleep or wake. FIG. 9 illustrates a flow chart for determining whether the human body is in the REM stage in the sleep awaking method. As shown in FIG. 9, in the step 32, acceleration signals at individual times within the REM determining period are obtained, variations G of acceleration signals at adjacent times are calculated, the variations G with a threshold G' for the variations of the acceleration signals are compared one by one, and whether the acceleration signals are periodic are determined, if at least one variation G is larger than the threshold G' for the variations of the acceleration signals at adjacent times and/or the variation of the acceleration signals is not periodic, it is determined that the human body is in the REM stage and the step S4 is entered, and if all the variations G are smaller than or equal to the threshold G' for the variations of the acceleration signals at adjacent times and the variation of the acceleration signals is periodic, it is determined that the human body is not in the REM stage and the step S5 is entered.

Alternatively, in the determination procedure described in the above step S32, it is possible to add some determination conditions to improve the determination accuracy. For example, it is possible to calculate the variations M of heart rate signals at adjacent times within the REM determining period, compare the variations M of the heart rate signals with the threshold M' of the variations of the heart rate signals at adjacent times, and determine whether the variations M of the heart signals are periodic. When any one or more of the determination results of the four determinations that at least one $G > G'$, at least one $M > M'$, the variation of G is not periodic, and the variation of M is not periodic is true, it is determined to be the REM stage. When all the determination results of the four determinations that all $G \leq G'$, all $M \leq M'$, the variation of G is periodic, and the variation of M is periodic are true, it is determined to be the non-REM stage. As another example, it is also possible to add a determination condition related to body temperature (details can refer to the above related descriptions on the sleep awaking system of embodiments of the present disclosure) to further improve the accuracy of the determination on whether the human body is in the REM stage.

It is noted that the time length of the REM determining period can be optionally 8 minutes~12 minutes, or can be 10 minutes. The users can also set the time length according to their own conditions.

In the present embodiment, the time length from the REM determining time to the awaking time can exemplarily be equal to the sum of the REM determining period and the pre-awaking period. For the light awaking manner, an awaking buffering period can be included after the REM determining period and the pre-awaking period pass in turn from the REM determining time to the awaking time, that is, the time length from the REM determining time to the awaking time is equal to the sum of the REM determining period, the pre-awaking period and the awaking buffering period.

In the following, detailed description will be made on a sleep awaking method incorporating the light awaking manner.

Figure 10:
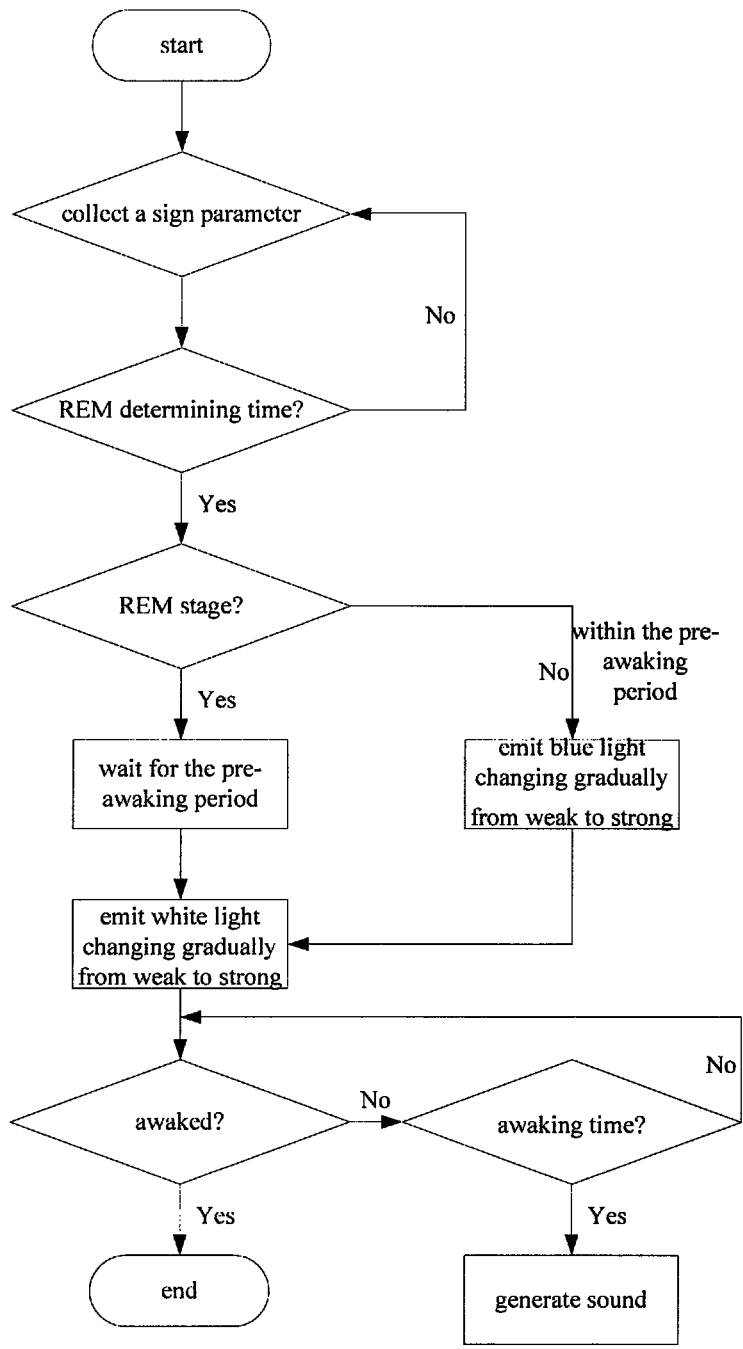
FIG. 10 is a flowchart comprising an awaking mechanism of a sleep awaking method provided by an embodiment of the present disclosure.

FIG. 10 is a flowchart comprising an awaking mechanism of a sleep awaking method provided by an embodiment of the present disclosure. As shown in FIG. 10, the step S4 can exemplarily comprise: emitting white light changing gradually from weak to strong within the awaking buffering period after the pre-awaking period until the human body is awaked or the awaking buffering period is over, and stopping emitting the white light changing gradually from weak to strong then; and generating a sound to awake the human body if the human body is not awaked at the end of the awaking buffering period.

It is noted that, in the above step, the determination on whether the human body is in the sleep or wake state can be continuously performed during the emitting of the white light. If it is determined that the human body is in the sleep state, the white light is continuously emitted until it is determined that the human body is in the wake state, and then the emitting of the white light is stopped to make the system stop operating. If the human body is still in the sleep state after the awaking buffering period is over, then the emitting of the white light has to be stopped and sound is generated at the same time to force the human body to wake up.

The step S5 can exemplarily comprise: emitting blue light changing gradually from weak to strong within the pre-awaking period to cause the human body to enter the REM stage until the pre-awaking period is over, and stopping emitting the blue light changing gradually from weak to strong then; emitting white light changing gradually from weak to strong within the awaking buffering period until the human body is awaked or the awaking buffering period is over, and stopping emitting the white light changing gradually from weak to strong then; and generating a sound to awake the human body if the human body is not awaked at the end of the awaking buffering period.

In addition, when determining that the human body is not in the REM stage, it is needed to cause the human body to enter the REM stage by some means. In the above step, a manner of emitting blue light changing gradually from weak to strong is adopted to lead the human body to the REM stage gradually. After the operation of causing to enter the REM stage with the time length being the pre-awaking period is performed, the white light changing gradually from weak to strong is emitted to awake the human body. If the human body is not awaked after the awaking buffering period is over, then the sound is used to force the human body to wake up.

It is noted that the time lengths of the awaking buffering period and the pre-awaking period are not specifically defined, but can be set according to practical situations. The time length of the pre-awaking period can exemplarily be 15 minutes~25 minutes, or can also be 20 minutes, in order to ensure the human body can enter the REM stage within this period as far as possible. The time length of the awaking buffering period can exemplarily be 10 minutes~20 minutes, and can also be 15 minutes, to ensure the light can be used to awake the human body gradually.

The above descriptions are only specific implementations of the present disclosure, but the protection scope of the present disclosure is not limited to this. Changes or replacements that can be easily devised by those skilled in the art within the technical scope of the present disclosure should all fall within the protection scope of the present disclosure. Therefore, the protection scope of the present disclosure should be defined by the protection scope of the claims.

The present application claims the priority of Chinese Patent Application No. 201410489808.0 filed on Sep. 23, 2014, entire content of which is incorporated herein as part of the present application by reference.

What is claimed is:

1. A sleep awaking system comprising:
   a sign parameter collecting module configured to collecting a sign parameter of a human body;
   a time determining module configured to determining whether a present time is a REM determining time;
   a REM determining module configured to obtaining the sign parameter and determining whether the human body is in a REM stage according to the sign parameter in a REM determining period when the time determining module determines that the present time is the REM determining time;
   an awaking module configured to awaking the human body after a pre-awaking period when the REM determining module determines that the human body is in the REM stage, and causing the human body to enter the REM stage within the pre-awaking period and awaking the human body after the pre-awaking period when the REM determining module determines that the human body is not in the REM stage,
   wherein the REM determining period and the pre-awaking period pass in turn from the REM determining time to the awaking time, and
   wherein the human body is determined to be in the REM stage in a case where a total variation of acceleration signals of respective times within the REM determining period is smaller than or equal to a first threshold, and at least one variation of acceleration signal at adjacent times within the REM determining period is larger than a second threshold.

2. The sleep awaking system according to claim 1, wherein the sign parameter collecting module comprises an acceleration collecting unit configured to collecting acceleration signals of body movement.

3. The sleep awaking system according to claim 1, wherein the REM determining module comprises:
   a sleep/wake determining unit configured to obtaining acceleration signals of respective times within the REM determining period when the time determining module determines that the present time is the REM determining time, calculating the total variation of the acceleration signals within the REM determining period, and comparing the total variation of the acceleration signals with a threshold for the total variation of the acceleration signals within the REM determining period, determining that the human body is in a sleep state when the total variation of the acceleration signals is smaller than or equal to the threshold for the total variation of the acceleration signals, and determining that the human body is in a wake state when the total variation of the acceleration signals is larger than the threshold for the total variation of the acceleration signals; and a REM determining unit configured to calculating variations of acceleration signals at adjacent times within the REM determining period, when the sleep/wake determining unit determines that the human body is in the sleep state, comparing the variations of the acceleration signals with a threshold for the variations of the acceleration signals one by one, and determining whether variation of the acceleration signals is periodic, determining that the human body is in the REM stage when at least one variation of the acceleration signals is larger than the threshold for the variations of the acceleration signals at adjacent times and/or the variation of the acceleration signals is not periodic, and determining that the human body is not in the REM stage when all the variations of the acceleration signals are smaller than or equal to the threshold for the variations of the acceleration signals at adjacent times and the variation of the acceleration signals is periodic.

4. The sleep awaking system according to claim 3, wherein the sign parameter collecting module further comprises a heart rate collecting unit configured to collecting heart rate signals;

the sleep/wake determining gait of the REM determining module is configured to obtain heart rate signals of respective times within the REM determining period when the time determining module determines that the present time is the REM determining time, calculate the average of the heart rate signals within the REM determining period, compare the average of the heart rate signals with a threshold for the average of the heart rate signals within the REM determining period, determine that the human body is in the sleep state when the average of the heart rate signals is smaller than or equal to the threshold for the average of the heart rate signals and the total variation of the acceleration signals is smaller than or equal to the threshold for the e total variation of the acceleration signals, and determine that the human body is in a wake state when the average of the heart rate signals is larger than the threshold for the average of the heart rate signals and/or the total variation of the acceleration signals is larger than the threshold for the total variation of the acceleration signals; and the REM determining unit of the REM determining module is configured to calculate variations of the heart rate signals at adjacent times within the REM determining period when the sleep/wake determining unit determines that the human body is in the seep state, compare the variations of the heart rate signals with a threshold for the variations of the heart rate signals at adjacent times one by one, and determine whether variation of the heart rate signals is periodic, determine the human body is in the REM stage when any one or more of the determination results of the four determinations that at least one variation of the heart rate signals is larger than the threshold for the variations of the heart rate signals at adjacent times, that the variation of the heart rate signals is not periodic, that at least one variation of the acceleration signals is larger than the threshold for the variations of the acceleration signals at adjacent times and that the variation of the acceleration signals is not periodic is true, and determine that the human body is not in the REM stage when all the variations of the heart rate signals are smaller than or equal to the threshold for the variations of the heart rate signals at adjacent times, all the variations of the acceleration signals are smaller than or equal to the threshold for the variations of the acceleration signals at adjacent times, and the variation of the heart rate signals and the variation of the acceleration signals are both periodic.

5. The sleep awaking system according to claim 3, wherein the sign parameter collecting module further comprises a body temperature collecting unit configured to collecting body temperature signals; and the REM determining unit of the REM determining module is configured to obtain a variation curve of the body temperature signals with respect to time within the REM determining period when the time determining module determines that the present time is the REM determining time, calculate a difference degree between the variation curve of the body temperature signals with respect to time and the ideal variation curve of the body temperature signals of the human body in the REM stage with respective to time, determine the human body is in the REM stage when any one or more of the determination results of the five determinations that the difference degree is smaller than or equal to a threshold for the difference degree, that at least one variation of the acceleration signals is larger than the threshold for the variations of the acceleration signals at adjacent times, that the variation of the acceleration signals is not periodic, that at least one variation of the heart rate signals is larger than the threshold for the variations of the heart rate signals at adjacent times and that the variation of the heart rate signals is not periodic is true, and determine that the human body is not in the REM stage when the difference degree is larger than the threshold for the difference degree, all the variations of the acceleration signals are smaller than or equal to the threshold for the variations of the acceleration signals at adjacent times, all the variations of the heart rate signals are smaller than or equal to the threshold for the variations of the heart rate signals at adjacent times, and the variation of the heart rate signals and the variation of the acceleration signals are both periodic.

6. The sleep awaking system according to claim 3, wherein an awaking buffering period is included after the REM determining period and the pre-awaking period pass in turn from the REM determining time to the awaking time, and the time length from the REM determining time to the awaking time is equal to the sum of the REM determining period, the pre-awaking period and the awaking buffering period.

7. The sleep awaking system according to claim 6, wherein the awaking module comprises:

a white light emitting unit configured to emitting white light changing gradually from weak to strong within the awaking buffering period after the pre-awaking period until the human body is awaked or the awaking buffering period is over and stopping emitting the white light changing gradually from weak to strong then;

a blue light emitting unit configured to emitting blue light changing gradually from weak to strong within the pre-awaking period when the REM determining module determines that the human body is not in the REM stage to cause the human body to enter the REM stage until the pre-awaking period is over, and stopping emitting the blue light changing gradually from weak to strong then;

a sound generating unit configured to generating a sound to awake the human body when the human body is not awaked at the end of the awaking buffering period.

8. The sleep awaking system according to claim 7, wherein the sleep/wake determining unit of the REM determining module is also configured to determine whether the human body is in the sleep state or the wake state within the awaking buffering period, and trigger the white light emitting unit to stop emitting the white light changing gradually from weak to strong when it is determined that the human body is in the wake state.

9. The sleep awaking system according to claim 6, wherein the time length of the REM determining period is 8 minutes~12 minutes, the time length of the pre-awaking period is 15 minutes~25 minutes, and the time length of the awaking buffering period is 10 minutes~20 minutes.

10. The sleep awaking system according to claim 1, wherein the time length from the REM determining time to the awaking time is equal to the sum of the REM determining period and the pre-awaking period.

11. A sleep awaking method comprising:
a step S1 of collecting a sign parameter of a human body;
a step S2 of determining whether a present time is a REM determining time, and entering a step S3 if yes;
the step S3 of obtaining the sign parameter, determining whether the human body is in a REM stage according to the sign parameter within the REM determining period, entering a step S4 if yes, and entering a step S5 if no;
the step S4 of awaking the human body after a pre-awaking period;
the step S5 of causing the human body to enter the REM stage within the pre-awaking period, and awaking the human body after the pre-awaking period,
wherein the REM determining period and the pre-awaking period pass in turn from the REM determining time to the awaking time, and
wherein the human body is determined to be in the REM stage in a case where a total variation of acceleration signals of respective times within the REM determining period is smaller than or equal to a first threshold, and at least one variation of acceleration signal at adjacent times within the REM determining period is larger than a second threshold.

12. The sleep awaking method according to claim 11, wherein the step S1 comprises collecting acceleration signals of body movement.

13. The sleep awaking method according to claim 12, wherein the step S3 comprises:
a step S31 of obtaining acceleration signals of respective times within the REM determining period, calculating the total variation of the acceleration signals within the REM determining period, comparing the total variation of the acceleration signals with a threshold for the total variation of the acceleration signals within the REM determining period, determining that the human body is in a sleep state and entering a step S32 if the total variation of the acceleration signals is smaller than or equal to the threshold for the total variation of the acceleration signals, and determining that the human body is in a wake state if the total variation of the acceleration signals is larger than the threshold for the total variation of the acceleration signals; and
the step S32 of calculating variations of acceleration signals at adjacent times within the REM determining period, comparing the variations of the acceleration signals with a threshold for the variations of the acceleration signals at adjacent times one by one, determining whether variation of the acceleration signals is periodic, determining that the human body is in the REM stage and entering the step S4 when at least one variation of the acceleration signals is larger than the threshold for the variations of the acceleration signals at adjacent times and/or the variation of the acceleration signals is not periodic, and determining that the human body is not in the REM stage and entering the step S5 when all the variations of the acceleration signals are smaller than or equal to the threshold for the variations of the acceleration signals at adjacent times and the variation of the acceleration signals is periodic.

14. The sleep awaking method according to claim 13, wherein the step S1 further comprises collecting heart rate signals;
the step S31 comprises: obtaining heart rate signals of respective times within the REM determining period, calculating the average of the heart rate signals within the REM determining period, comparing the average of the heart rate signals with a threshold for the average of the heart rate signals within the REM determining period, determining that the human body is in the sleep state and entering the step S32 if the average of the heart rate signals is smaller than or equal to the threshold for the average of the heart rate signals and the total variation of the acceleration signals is smaller than or equal to the threshold for the total variation of the acceleration signals, and determine that the human body is in a wake state if the average of the heart rate signals is larger than the threshold for the average of the heart rate signals and/or the total variation of the acceleration signals is larger than the threshold for the total variation of the acceleration signals; and
the step S32 comprises: calculating variations of the heart rate signals at adjacent times within the REM determining period, comparing the variations of the heart rate signals with a threshold for the variations of the heart rate signals at adjacent times one by one, determining whether variation of the heart rate signals is periodic, determining that the human body is in the REM stage and entering the step S4 if any one or more of the determination results of the four determinations that at least one variation of the heart rate signals is larger than the threshold for the variations of the heart rate signals at adjacent times, that the variation of the heart rate signals is not periodic, that at least one variation of the acceleration signals is larger than the threshold for the variations of the acceleration signals at adjacent times and that the variation of the acceleration signals is not periodic is true, and determining that the human body is not in the REM stage and entering the step S5 if all the variations of the heart rate signals are smaller than or equal to the threshold for the variations of the heart rate signals at adjacent times, all the variations of the acceleration signals are smaller than or equal to the threshold for the variations of the acceleration signals at adjacent times, and the variation of the heart rate signals and the variation of the acceleration signals are both periodic.

15. The sleep awaking method according to claim 14, wherein the step S1 further comprises collecting body temperature signals; and
the step S32 comprises: obtaining a variation curve of the body temperature signals with respect to time within the REM determining period, calculating a difference degree between the variation curve of the body temperature signals with respect to time and the ideal variation curve of the body temperature signals of the human body in the REM stage with respective to time, determining the human body is in the REM stage and entering the step S4 if any one or more of the determination results of the five determinations that the difference degree is smaller than or equal to a threshold for the difference degree, that at least one variation of the acceleration signals is larger than the threshold for the variations of the acceleration signals at adjacent times, that the variation of the acceleration signals is not periodic, that at least one variation of the heart rate signals is larger than the threshold for the variations of the heart rate signals at adjacent times and that the variation of the heart rate signals is not periodic is true, and determine that the human body is not in the REM stage and entering the step S5 if the difference degree is larger than the threshold for the difference degree, all the variations of the acceleration signals are smaller than or equal to the threshold for the variations of the acceleration signals at adjacent times, all the variations of the heart rate signals are smaller than or equal to the threshold for the variations of the heart rate signals at adjacent times, and the variation of the heart rate signals and the variation of the acceleration signals are both periodic.

16. The sleep awaking method according to claim 13, wherein an awaking buffering period is included after the REM determining period and the pre-awaking period pass in turn from the REM determining time to the awaking time, the time length from the REM determining time to the awaking time is equal to the sum of the REM determining period, the pre-awaking period and the awaking buffering period.

17. The sleep awaking method according to claim 16, wherein the step S4 comprises: emitting white light changing gradually from weak to strong within the awaking buffering period after the pre-awaking period until the human body is awaked or the awaking buffering period is over and stopping emitting the white light changing gradually from weak to strong then; and generating a sound to awake the human body if the human body is not awaked at the end of the awaking buffering period;

the step S5 comprises: emitting blue light changing gradually from weak to strong within the pre-awaking period to cause the human body to enter the REM stage until the pre-awaking period is over, and stopping emitting the blue light changing gradually from weak to strong then; emitting white light changing gradually from weak to strong within the awaking buffering period until the human body is awaked or the awaking buffering period is over and stopping emitting the white light changing gradually from weak to strong then; and generating a sound to awake the human body if the human body is not awaked at the end of the awaking buffering period.

18. The sleep awaking method according to claim 17, wherein the step S4 further comprises: determining whether the human body is in the sleep state or the wake state within the awaking buffering period, and stopping emitting the white light changing gradually from weak to strong when it is determined that the human body is in the wake state.

19. The sleep awaking method according to claim 16, wherein the time length of the REM determining period is 8 minutes~12 minutes, the time length of the pre-awaking period is 15 minutes~25 minutes, and the time length of the awaking buffering period is 10 minutes~20 minutes.

20. The sleep awaking system according to claim 11, wherein the time length from the REM determining time to the awaking time is equal to the sum of the REM determining period and the pre-awaking period.

* * * * *